United States Patent
Wucher

(10) Patent No.: US 9,433,478 B2
(45) Date of Patent: Sep. 6, 2016

(54) ORTHODONTIC APPARATUS

(71) Applicant: STELLENBOSCH UNIVERSITY, Stellenbosch (ZA)

(72) Inventor: Tim Wucher, Stellenbosch (ZA)

(73) Assignee: ORTHO FUTURE TECHNOLOGIES (PTY) LTD, Klein Windhoek, Windhoek (NA)

( * ) Notice: Subject to any disclaimer, the term of this patent is extended or adjusted under 35 U.S.C. 154(b) by 274 days.

(21) Appl. No.: 14/378,871

(22) PCT Filed: Feb. 1, 2013

(86) PCT No.: PCT/IB2013/050856
§ 371 (c)(1),
(2) Date: Aug. 14, 2014

(87) PCT Pub. No.: WO2013/121316
PCT Pub. Date: Aug. 22, 2013

(65) Prior Publication Data
US 2015/0230885 A1    Aug. 20, 2015

(30) Foreign Application Priority Data
Feb. 15, 2012   (ZA) ................................. 2012/01102

(51) Int. Cl.
*A61C 7/00*    (2006.01)
(52) U.S. Cl.
CPC ..................................... *A61C 7/008* (2013.01)
(58) Field of Classification Search
CPC ...................................................... A61C 7/008
See application file for complete search history.

(56) References Cited

U.S. PATENT DOCUMENTS

| | | | | |
|---|---|---|---|---|
| 6,832,912 B2* | 12/2004 | Mao | ......................... | A61C 7/22 433/24 |
| 7,029,276 B2* | 4/2006 | Mao | ......................... | A61C 7/22 433/24 |
| 2008/0227046 A1* | 9/2008 | Lowe | ....................... | A61C 7/00 433/2 |
| 2009/0042159 A1 | 2/2009 | Yamamoto et al. | | |
| 2011/0136070 A1 | 6/2011 | Rubin et al. | | |
| 2013/0273490 A1* | 10/2013 | Way | ....................... | A61C 7/008 433/6 |
| 2015/0173856 A1* | 6/2015 | Lowe | ..................... | A61C 7/008 433/24 |
| 2015/0265375 A1* | 9/2015 | Yamamoto | ............. | A61C 7/008 433/2 |

OTHER PUBLICATIONS

International Search Report dated Jun. 6, 2013 for Application No. PCT/IB2013/050856.

* cited by examiner

*Primary Examiner* — Ralph Lewis
(74) *Attorney, Agent, or Firm* — Ladas & Parry LLP

(57) ABSTRACT

A medical apparatus for use in the corrective treatment of malocclusion and other dentofacial defects is provided. The apparatus has at least one stimulator which is configured to apply a stimulus to a part of the dento-oral complex and includes at least one actuator controllable by means of electronic signals. A feedback system is also provided and is configured to measure parameters relating to the biomechanical tissue response resulting from the stimulus applied by the at least one stimulator, to analyze the parameters by means of a processor, and to adjust the stimulus applied by the at least one stimulator by means of the required control signals in order to apply a stimulus representing an optimal orthodontic force.

18 Claims, 6 Drawing Sheets

ORTHODONTIC APPARATUS

RELATED APPLICATION

This application is an application under 35 U.S.C. 371 of International Application No. PCT/IB2013/050856 filed on Feb. 1, 2013, the entire contents of which are incorporated herein by reference.

FIELD OF THE INVENTION

This invention relates to orthodontic devices. More specifically, the invention relates to a medical apparatus for use in the corrective treatment of malocclusion and other dentofacial defects.

BACKGROUND TO THE INVENTION

Orthodontics is the branch of dentistry that deals with the prevention or correction of irregularities of the teeth and jaws. These irregularities may affect the oral health, as well as possibly the physical, aesthetic and/or mental wellbeing of affected individuals.

Tooth positioning and orofacial bone structures can currently be altered using manual, mechanical systems, generally consisting of a combination of, for example, wires, brackets, bands, chains, springs and elastics, a system commonly referred to as "dental braces" or simply "braces". Braces are commonly used to generate, transmit and maintain forces, force vectors and moments to individual teeth or between teeth, activating various biomechanical processes within the affected tissues to facilitate tooth movement.

It is generally accepted that a force of zero magnitude will not induce any tooth movement, whereas a force of excessive magnitude might damage cells surrounding the tooth and may also cause root resorption and excessive patient discomfort. This gives rise to the concept that an optimal force exists, between a zero force and a force of excessive magnitude, which would be capable of inducing the maximum rate of tooth movement without causing any tissue damage, root resorption, as little as possible patient discomfort, and a minimum level of additional, adverse side-effects.

Conventional orthodontic systems have a number of shortcomings with regard to this optimal orthodontic force. Firstly, the majority of orthodontic systems rely purely on mechanical components, which are relatively inflexible once put in place. The placement of the mechanical components by the practitioner largely determines the forces exerted on the teeth and virtually no controlled changes can be made thereto without manually changing the configuration of the mechanical components. Furthermore, many of the components used, which as stated above include, amongst others, springs, wires and elastic bands, do not accurately generate a constant desired force over a longer period of time or over a specified distance, largely due to the physical characteristics of these components. This makes it improbable that the forces transmitted to the teeth are representative of the optimal force for any continuous period of time. The result of other than optimal forces being applied to the orofacial structures can induce the problems mentioned above.

The problems mentioned above may, however, not be the biggest concern regarding the treatment of, for example, malocclusion and other abnormalities of the orofacial structures. Equally important is the need to accurately determine the optimal force that would result in the most effective treatment, as this optimal force may differ from patient to patient. To the applicant's knowledge, it has not yet been possible to quantitatively describe such an optimal force. Numerous attempts have been made to describe a universally applicable relationship between force magnitude and the resultant rate of tooth movement, but current scientific wisdom seems to suggest that these relationships are much more appropriately determined on an individual basis or even on a tooth-specific basis for a given patient.

Based on the data from a number of studies of which the applicant is aware, it was concluded that the reviewed experimental results were negatively affected by, amongst others, the inability to accurately calculate stresses in the periodontal ligament of a given tooth, the inability to control the type of tooth movement, the different phases of tooth movement during an applied force and large inter-individual variations or even variations within individuals. As a result, no exact ideal force magnitude could be recommended.

It has also been found that large individual variations exist for the mean rate of tooth movement achieved under application of the same forces. A possible explanation that has been proposed for this phenomenon is that each individual could have his or her own optimal force that would produce the maximum rate of tooth movement.

More recently, the view has been adopted that the movement of teeth is a result of externally applied mechanical stimuli and the subsequent biological reactions that take place within the periodontium. Inherent to the mechanical stimuli are various parameters including the force magnitude, direction, point of application, frequency of application and duration of application. Still further parameters could play an important role when non-static forces are considered such as the force profile, oscillatory frequency and oscillatory amplitude. The above parameters in combination with the anatomical and physiological properties inherent to the affected tooth/teeth lead to yet further factors affecting tooth movement. A certain mechanical stimulus applied to a specific case will lead to cellular strains, shear stresses and pressure changes within the affected tissues. Each of these could further affect the resulting tooth movement thereby emphasizing the importance of the externally applied stimulus.

The effect of unidirectional micro currents on the rate of tooth movement has also been studied by the application of a low-frequency pulsating force. It was found that the rate of movement for the tooth to which a pulsing force was applied was greater than that of a control tooth in the same individual.

It is clear that the force magnitude is not the only factor affecting the rate of tooth movement and that various other factors exist that need to be taken into consideration and controlled to induce the maximum rate of tooth movement. The optimal orthodontic force can then be described as the force that, to the best of scientific knowledge, is most effective in producing a desired outcome of a certain orthodontic treatment. This may be the force that, if applied to one or multiple teeth, would result in the maximum rate of tooth movement, while at the same time avoiding any adverse short or long term tissue damage, minimising patient discomfort or aiding in achieving any other desired outcomes. The force can be in any direction or around any axis in a three dimensional space and can vary in magnitude, direction, frequency, profile or point of application. The optimal orthodontic force can be patient specific, as well as age or health specific, and can further differ for each tooth, group of teeth, type of tooth movement or other type of treatment.

In the remainder of this specification the term "optimal orthodontic force" should be interpreted to be such an optimal force when applied in an orthodontic environment. The term "optimal force" should in turn be interpreted to have a corresponding meaning but capable of being applied in any reconstructive or corrective surgery where relative bone or tissue movement is achieved by means of the application of a mechanical force or moment over a period of time. In addition, the terms "force" and "stimulus" are used interchangeably and should be interpreted broadly to include any combination of forces and moments or either individually.

SUMMARY OF THE INVENTION

In accordance with this invention there is provided a medical apparatus for use in the corrective treatment of malocclusion or other dento-facial defects comprising:
- at least one stimulator configured to apply a stimulus to a part of the dento-oral complex utilising at least one actuator, the actuator being controllable by means of electronic control signals;
- attachment formations configured to secure the at least one stimulator to the part of the dento-oral complex;
- a feedback system including at least one sensor configured to measure parameters relating to biomechanical tissue response resulting from the stimulus applied by the stimulator;
- a power source configured to provide power to the apparatus; and
- a processor in data communication with the stimulator and feedback system, the processor being configured to receive the parameters from the feedback system, to adjust the control signals based at least to some extent on the parameters, and to transmit the adjusted control signals to the stimulator so that the stimulus applied by the stimulator as a result of the adjusted control signals are increasingly representative of an optimal orthodontic force.

Further features of the invention provide for the control signals to cause the stimulator to apply stimuli varying in one or more of magnitude, frequency, direction, duration and point of application, or a combination of these; for the at least one sensor to be configured to sense a change in pressure, force or position of a tooth or other part of the dento-oral complex; and for the at least one sensor to be configured to sense a change in tooth movement occurring over a period of time.

A still further feature of the invention provides for the processor to include a memory module in data communication with it and on which is stored software configured to cause the processor to receive parameters from the sensors, to store and process the parameters, to adjust the control signals and to transmit the control signals to the stimulator.

Yet further features of the invention provide for apparatus to include a communication module enabling it to communicate with an external processor; for the communication module to be configured to communicate over a local area or wide area network or the Internet; for the communications module to be to be connectable to a communications network with of one or more of a Universal Serial Bus port, an infra-red module, a Bluetooth module and a near-field communication module; for the software to be uploaded to the memory module by means of the communication module; for parameters received by the processor and stored on the memory module to be uploaded to a computer via the communication module; and for the parameters to be uploaded to a remote database associated with the computer for archiving and/or further processing.

Further features of the invention provide for any number of the components of the apparatus to be provided with waterproof, protective housings; and for the housings to be adapted to enable the apparatus to operate intra-orally.

Still further features of the invention provide for the apparatus to be used for an initial analysis of a patient's mouth, after which it is removed from the patient's mouth and replaced with an alternative apparatus; and for setup of the alternative apparatus to be done with data gathered from the initial analysis.

Yet further features of the invention provide for the power source and processor to be detachable from the apparatus; for at least one actuator to be configured to exert a stable, constant force when the power source or the processor has been detached; and for the power source and/or procession to be located intra- or extra-orally.

Even further features of the invention provide for the processor to be further configured to monitor and record the parameters over a period of time and for a number of different stimuli, and to determine an optimal orthodontic force based at least partially on the recorded parameters and their corresponding applied forces and moments.

The invention also provides a system for use in the corrective treatment of malocclusion or other dento-facial defects comprising a plurality of medical apparatuses as defined above, wherein the plurality of medical apparatuses are controlled by at least one central processor.

A further feature of the invention provides for the system to include a central communications module operable to communicate recorded data to and from a remotely accessible system database.

The invention still further provides a method of determining an optimal force for application to a part of the dento-oral complex of a patient for the corrective treatment of malocclusion and other dento-facial defects, the method including the steps of:
- applying a stimulus to the part of the dento-oral complex of the patient; collecting with at least one sensor, parameters relating to the movement of the part of the dento-oral complex resulting from the application of the stimulus;
- transmitting the parameters to a processor in data communication with the at least one sensor;
- analysing the parameters with reference to a reference force profile stored in a memory associated with the processor;
- repeatedly adjusting the applied stimulus based on the analyses and collecting further parameters relating to the movement of the part of the dento-oral complex resulting from the application of the adjusted stimulus; and
- identifying the stimulus being applied as the optimal force if optimal movement of the part of the deto-oral complex is achieved by application of the stimulus.

The invention yet further provides a method of treating malocclusion and other dento-facial defects in patients in need of treatment, the method including the steps of:
- applying a predetermined stimulus to a part of the dento-oral complex of the patient;
- collecting with at least one sensor, parameters relating to the movement of the part of the dento-oral complex resulting from the application of the stimulus;
- transmitting the parameters to a processor in data communication with the at least one sensor;
- analysing the parameters with reference to a reference force profile stored in a memory associated with the processor; and repeatedly adjusting the applied stimulus based on the analyses and collecting further parameters relating to the movement of the part of the dento-oral complex resulting from the application of the adjusted stimulus until optimal movement of the part of the dento-oral complex to which the stimulus is applied is achieved.

DETAILED DESCRIPTION WITH REFERENCE TO THE DRAWINGS

Figure 1:
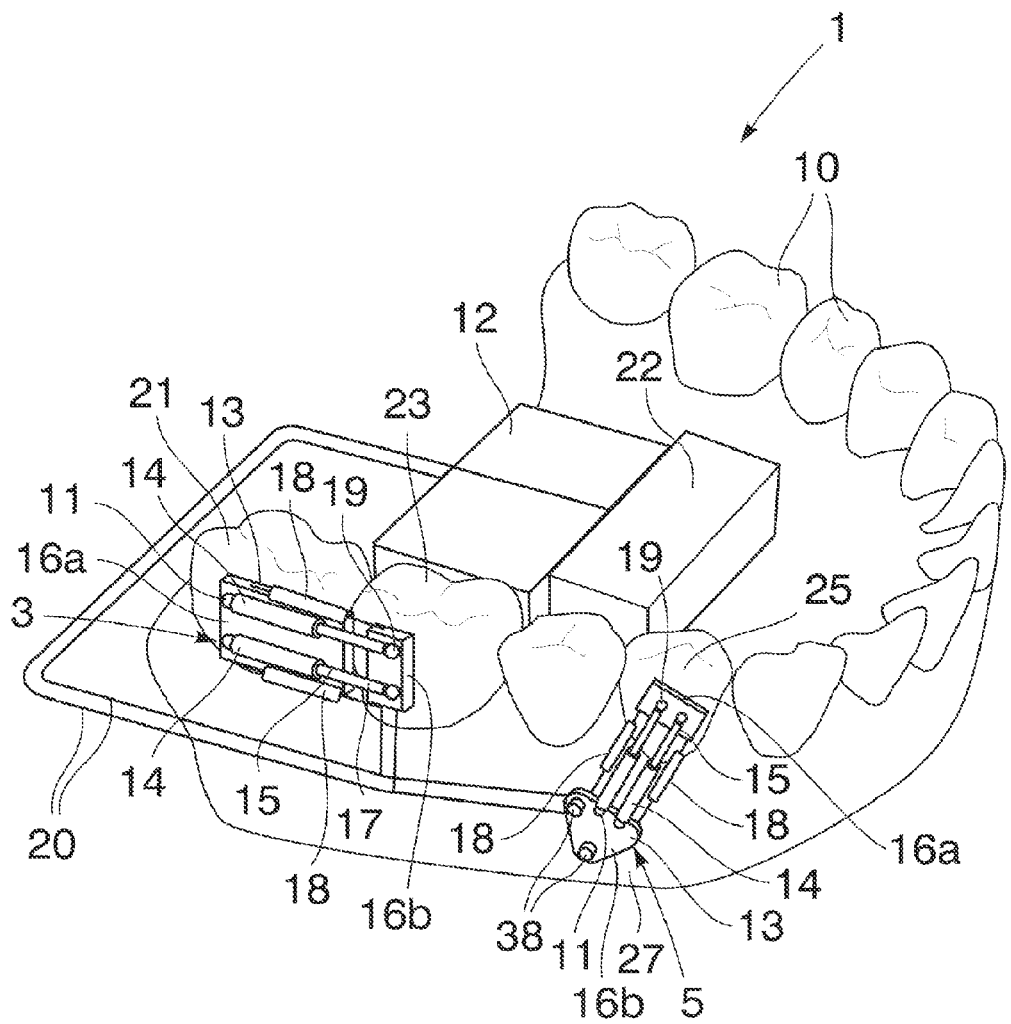
FIG. 1 is a representation of a medical apparatus in accordance with the invention, secured to a lower jaw of a patient.

A medical apparatus (1) for use in the corrective treatment of malocclusion and other dento-facial defects is shown in FIG. 1. In the figure, the apparatus (1) is used for corrective treatment of malocclusion and includes two portions (3, 5) each including two stimulators (14) and a feedback system including two sensors (18). Each portion (3, 5) of the apparatus includes a base (13) to which one end (11) of each stimulator (14) is secured. Each stimulator (14) includes an electronic linear actuator (15) including a mechanical arm (17) capable of extending and contracting along its major axis. The ends (11, 19) of each actuator (15) are in turn secured to mounting plates (16), which in turn are attached to parts of the dento-oral complex of the patient in need of treatment with attachment formations, between which parts forces are to be applied. The mounting plates comprise two distinct, cooperating portions (16*a*, 16*b*), configured to secure the stimulators (14) between two different teeth or between a tooth and a portion of the jaw between which forces are to be applied. The stimulators (14) and sensors (18) are electronically connected to a processor (12) and a power source (22) by means of an electronic circuit (20).

The apparatus (1) is shown in an operative position secured to teeth (21, 23, 25) on the lower jaw (27) of a patient, the first portion (3) between two adjacent teeth (21, 23) and the second portion (5) between a tooth (25) and the jaw (27) of the patient. While any suitable attachment formations for securing the mounting plates (16) of the portions (3, 5) to teeth or other parts of the dento-oral complex of a patient can be used, it is foreseen that temporary anchorage devices (TADS) (38) may be used to secure mounting plates (16) to the jaw bone of the patient. It should be appreciated that attachment formation may include suitable adhesives that are safe for intra-oral usage, dental cement and the like.

In use, the stimulators (14) are able to apply forces, moments or both to a tooth or other part of the dento-oral complex to which they are attached by individually extending or retracting the mechanical arms as required. The actuators (15), and in turn the mechanical arms (17), are independently controllable by means of electronic signals transmitted to them from the processor (12). The forces applied by the stimulators in response to the control signals could, for example, vary in magnitude, frequency, direction, duration and point of application.

The apparatus (1) could therefore be used to apply forces or moments between teeth (21, 23), as is the case with portion (3), or to individual teeth (25) if secured between the applicable tooth (25) and the jaw (27) of the patient, as is the case with portion (5). Alternatively, forces or moments can also be applied to specified groups of teeth. In combination, the two linear actuators could be used to generate various force vectors parallel to the median plane or moment vectors perpendicular to the median plane. Similarly, other configurations of linear actuators or a single actuator with multiple degrees of freedom could be used to generate the required forces, as well as force and moment vectors in any direction or around any axis in a three dimensional space. This has the advantage that important parameters used in orthodontics, such as the moment-force ratio, can be controlled without changing any of the components or their configuration.

It should immediately be apparent that the stimulator (14) could consist of any number of different actuators capable of applying a force or moment to a tooth or other part of the dento-oral complex. The actuators used by each stimulator (14) could also vary and could include micro-actuator or micro-electromechanical systems such as, for example, piezoelectric motors, magnetic motors or any other means capable of generating the desired stimulus. It is foreseen that the stimulator will be able to maintain the desired force for a prolonged period of time to ensure that tooth movement or bone remodelling can be induced over the period of application.

As mentioned above, the feedback system associated with each portion (3, 5) of the apparatus (1) includes two sensors (18) configured to measure parameters relating to the bio-mechanical tissue response resulting from the forces or moments exerted on the teeth (21, 23, 25) by means of the actuators (15). The sensors (18) could, for example, measure parameters relating to changes in pressure, force or position of the respective teeth or other part of the dento-oral complex to which they are secured. These change parameters could be measured over any period of time and are transmitted from the various sensors (18) back to the processor (12) by means of the circuit (20).

The processor (12) is in turn in data communication with the stimulator (14) and the feedback system and is configured to receive the change parameters sensed by the sensors (18) of the feedback system, as well as to store and process them. Typically, the processor (12) will include a microprocessor (not shown) and memory module (not shown), as well as other electronic components to facilitate the processing of received data, as well as communication with the stimulators and feedback system.

In use, the processor (12) is configured to transmit control signals to the stimulators (14), which in turn cause the actuators (15) to apply a predefined force or moment to the teeth to which they are connected. The forces and/or moments applied to each tooth in turn stimulate the periodontal ligament ("PDL") of the tooth, which causes the tooth to move in the required direction. Various parameters relating to the movement of the tooth are then collected by means of the sensors (18) and are transmitted back to the processor (12) over the electronic connectors (20). Once the parameters are received, the processor (12) stores them in the memory module and analyses them with reference to a reference force profile which is stored on the memory. The processor then adjusts the control signals based on the measured parameters so as to approach an optimal orthodontic force. The adjusted control signals in turn cause the actuators (15) to adjust the forces and/or moments they are applying in an attempt to achieve the optimal movement of the applicable tooth. In practice therefore, different forces may be applied by the stimulators over time and their effects on the teeth to which they are connected may be measured. The forces may then be incrementally adjusted so as to approach an optimal orthodontic force for the specific patient and also for a specific tooth of the patient.

The processor (12) may be able to execute software instructions stored on the memory module enabling it to interpret the received parameters, correlate them with stored data and/or algorithms representing force profiles of the patient, to determine the optimal force profile for the patient based on the received parameters, historical, stored parameters and/or the algorithms, to adjust the control signals to make appropriate adjustments to the forces applied by the actuators (15), and to transmit the adjusted control signals to the stimulators (14). The software stored on the memory module may therefore instruct the processor (12) to process data, execute commands, communicate with other electronic devices and control the electromechanical system as a whole. The software may be capable of integrating information from the stimulator (14) and feedback from the sensor (18) system to establish a relation between the stimulus and the resulting biomechanical response and, ultimately, to generate a force profile that approximates the optimal orthodontic force.

The software may also include instructions enabling the device to communicate with external electronic devices, such as remote computers, and to allow for bidirectional information exchange. Parameters that have been sensed by the feedback system and have been recorded may be uploaded to a computer to create a visual and user friendly representation thereof. The software may further be used to create a connection to a computer that enables the inspection of real-time data, so that the practitioner could continuously and immediately examine the effect of a varying stimulus on the affected tissue such as the extent of compression of the PDL.

The power source (22) is configured to provide power to the various components of the apparatus. The power source (22) may be in the form of a battery, which may be rechargeable or replaceable. The battery may also be fixed or removable from the apparatus. Alternatively, the power source (22) may be any connection to an external device, wired or wireless, such as a computer or any other electronic device capable of providing power to the appliance. It is also envisioned that the power source may be a self-winding mechanical mechanism.

It should also be noted that the various components of the apparatus may be required to be waterproof, or at least adapted to operate in intraoral conditions.

Figure 2:
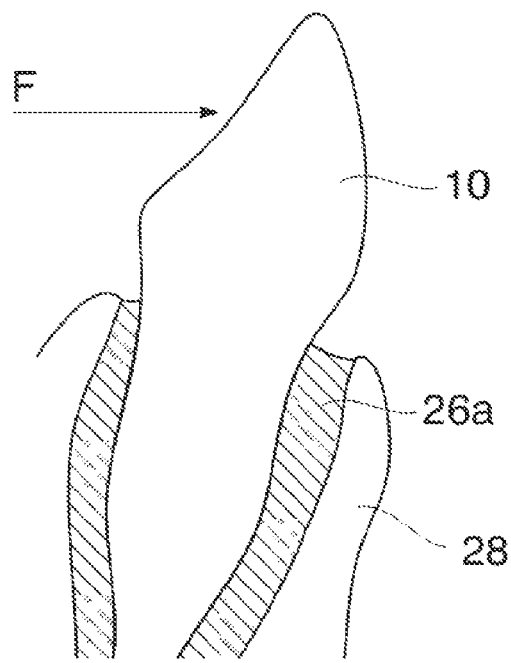
FIG. 2 is a side profile view of a tooth in a position before it has been moved by the apparatus.
Figure 3:
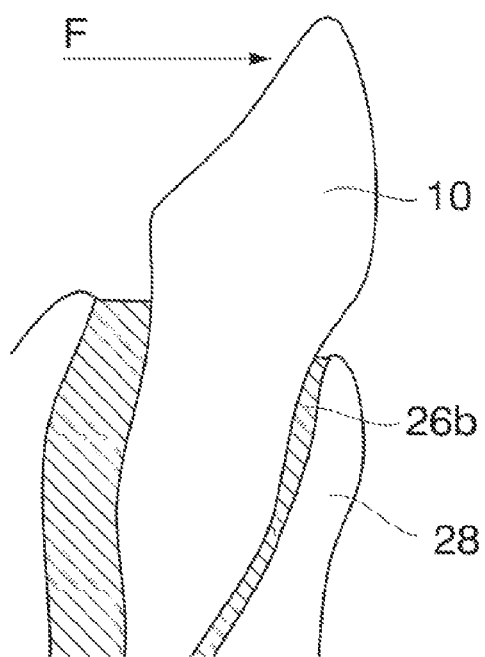
FIG. 3 is a side profile view of the tooth of FIG. 2 after it has been moved by the apparatus.

FIGS. 2 and 3 show the surrounding bone (28) of the dental alveolus into which a tooth (10) is attached by means of the PDL (26). The uncompressed PDL (26a) is shown in FIG. 2 and the compressed PDL (26b) in FIG. 3 resulting from a constant force (F) applied to the tooth (10) as shown.

Figure 4:
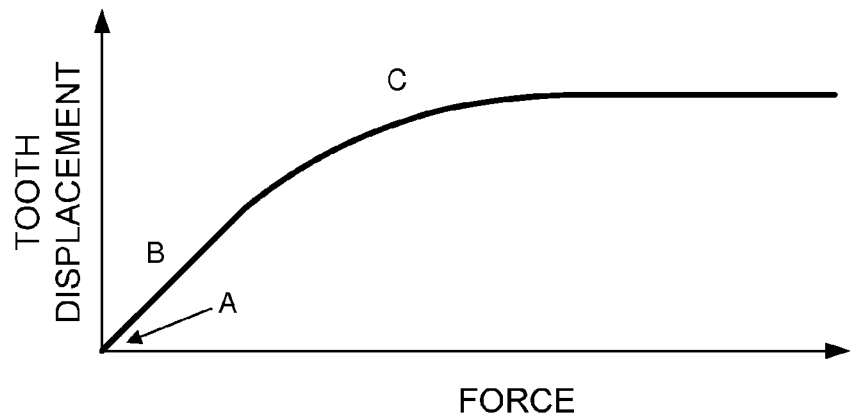
FIG. 4 is a graph illustrating the correlation between tooth displacement and force applied to the tooth.

FIG. 4 shows a graph of the force applied by the stimulator versus the displacement of a tooth to which the force is applied. It should be noted that applying a force with zero magnitude does not compress the PDL and would accordingly not stimulate any displacement of the tooth. This scenario corresponds to point A on the graph. If the force is increased, so would the measured displacement of the tooth as shown by point B. A still further increase in the applied force will eventually lead to the PDL being fully compressed, at which point the harder bone of the jaw will prevent further displacement of the tooth. This case corresponds to point C on the graph. It should be noted that the forces corresponding to points A and C on the graph will not induce the maximum rate of tooth movement. It can, however, reasonably be assumed that the force corresponding to the region surrounding point B on the graph causes a partially compressed PDL and thus is more likely to induce a higher rate of tooth movement.

Unlike conventional mechanical systems that are configured to apply a single, constant force to a tooth and wait for movement to occur, the apparatus of the present invention is capable of applying multiple, independent forces to the desired teeth, of receiving feedback relating to the consequential movement of the applicable teeth and to, based on electronic calculations, adjust the forces applied to the teeth to approximate forces that are most likely to induce the highest rate of tooth movement or are most effective in achieving any other desired outcome. Further, by the approximation of the optimal force magnitude, negative effects such as blood flow constriction, tissue damage, root resorption and the like may be at least partially avoided.

Figure 5:
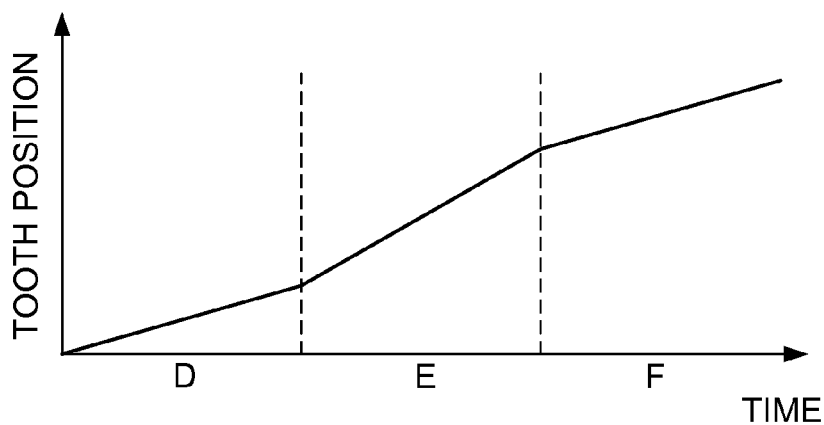
FIG. 5 is a graph illustrating relative tooth position over time.
Figure 6:
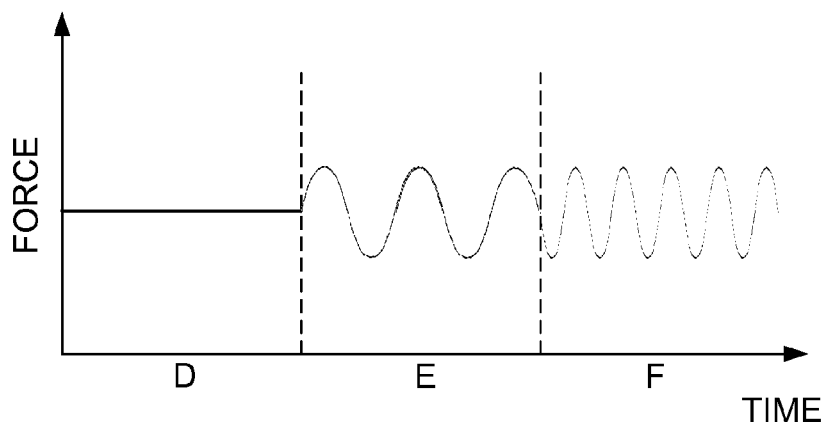
FIG. 6 is a graph illustrating the relative force applied over time to effect the relative tooth position of FIG. 5.

FIGS. 5 and 6 illustrate graphs representing further features of the apparatus. FIG. 6 shows three different force profiles that may be applied to a tooth during time intervals D, E and F, respectively. FIG. 5, in turn shows the feedback of a sensor associated with the tooth and corresponding to the tooth position as measured during the same time intervals. During time interval D, a constant force is applied to the tooth and is maintained for the duration of the interval, the constant force results in a change in the tooth position as shown in the corresponding time period of FIG. 5. During time interval E, a low frequency fluctuating force is applied to the same tooth as shown in FIG. 6, resulting in a further change in tooth position, but with a higher rate of tooth movement as again shown in the corresponding time period in FIG. 5. Finally, a high frequency fluctuating force is applied to the tooth during time interval F as can again be seen in FIG. 6, leading to an even further tooth displacement, however, at a lower rate of tooth movement.

It should be apparent that by monitoring the displacement of the tooth during the application of specific forces to the tooth, making use of the feedback provided by the sensors in the feedback system, to create data such as that presented in FIGS. 5 and 6, it may be possible to more accurately approximate a force that resembles the optimal orthodontic force for a specific tooth than was previously possible with conventional systems.

Figure 7:
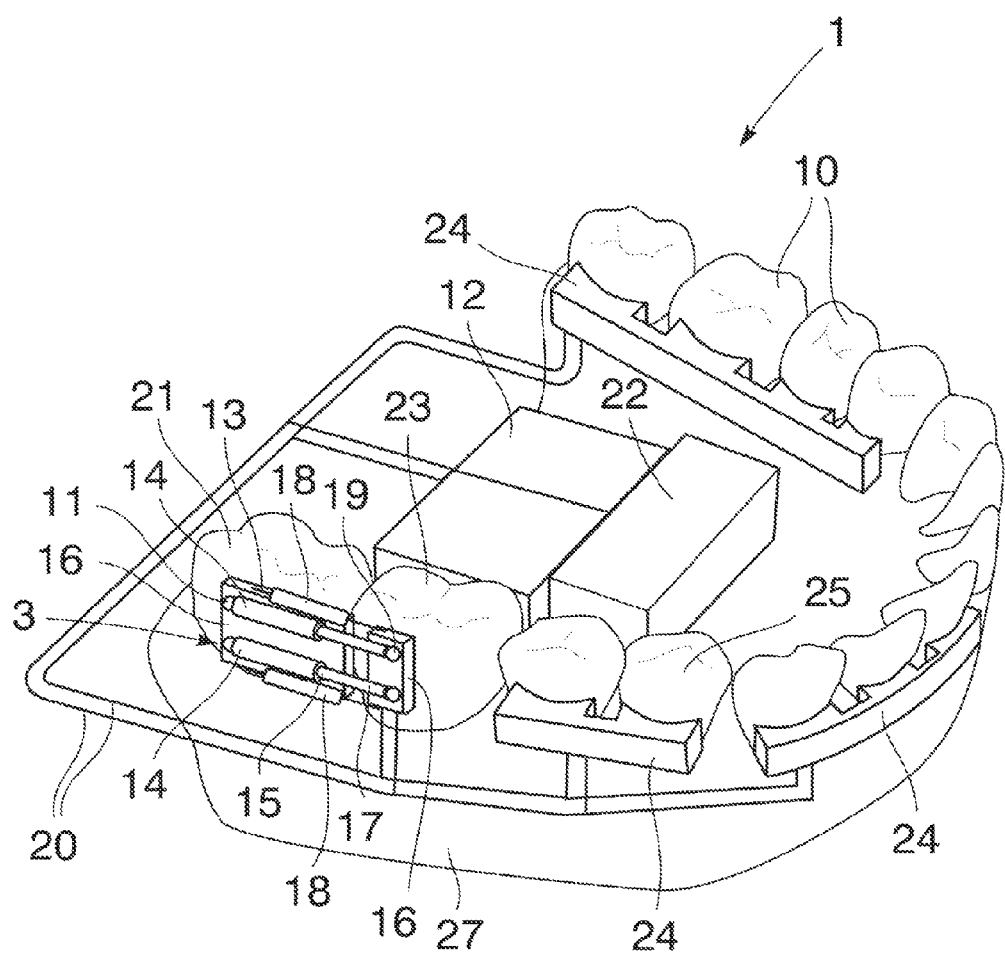
FIG. 7 is a representation of a further embodiment of the invention.

In the embodiment of the invention shown in FIG. 7, several stimulators (14) are attached to various parts of the dento-oral complex and are controlled by means of a central processor (12) and powered by means of a central power source (22). I the figure, like components to those described with reference to FIG. 1 above are indicated with like reference numerals. It should be appreciated that each stimulator (14) that forms part of the system (1) has at least one sensor (18) associated with it to measure and feed back the parameters relating to the movement of the various parts of the dento-oral complex to which they are attached, to the processor (12). A number of the stimulators are shown to have protective housings (24) secured over them so as to protect them, as well as the inside of the patient's mouth, against potential damage. In the embodiment shown, protective housings (24) can be seen on both the insides and the outsides of a patient's teeth. It should also be appreciated that apart from obscuring potentially sharp edges that may cause injury or irritation to the patient, the housings may also be manufactured from a suitably moisture impermeable substance, thereby also protecting the stimulators, actuators and sensors from moisture damage.

It is also foreseen that bi-directional information exchange between a dental system in accordance with the invention and a global database may be facilitated by software loaded on to the processor (12) if the system is also provided with a communications module (not shown). This may allow for data collected by the various portions of the system, each of which may be secured to a different part of the dento-oral complex, for a particular patient, to be uploaded and integrated with data associated with other patients. The correlated data may in turn be used in the development of improved general treatment models. These improved models may in turn be downloaded and used to further improve the functionality of individual apparatus. The operation of such an embodiment of the invention is shown in more detail in the diagram of FIG. 8. In the figure, the power source (22) provides power to all the portions of the system, appropriately secured to the dento-oral complex of a patient, each portion containing stimulators (14) and sensors and being secured to apply forces and moments to different teeth or other parts of a patient's mouth. The various portions, together with their feedback systems are in turn in communication with a central processing unit (12). The processing unit (12) is in turn in data communication with a computer system (30) by means of a communications module (not shown), which enables bi-directional information exchange between the processor (12) and the computer (30). It should be appreciated that the computer (30) may be positioned in close or relative proximity to the system when communication with the system is required, for example in a dental practitioner's practice, and that information may be uploaded to it when a patient visits the practice for a consultation.

The computer (30) is in turn configured to upload data to a global database (36). Data from such a database may again be downloaded and used to alter the operation of the apparatus at a later stage or to initiate force profiles which, from data aggregated from a variety of sources, are estimated to be close to optimal based on client criteria.

Figure 8:
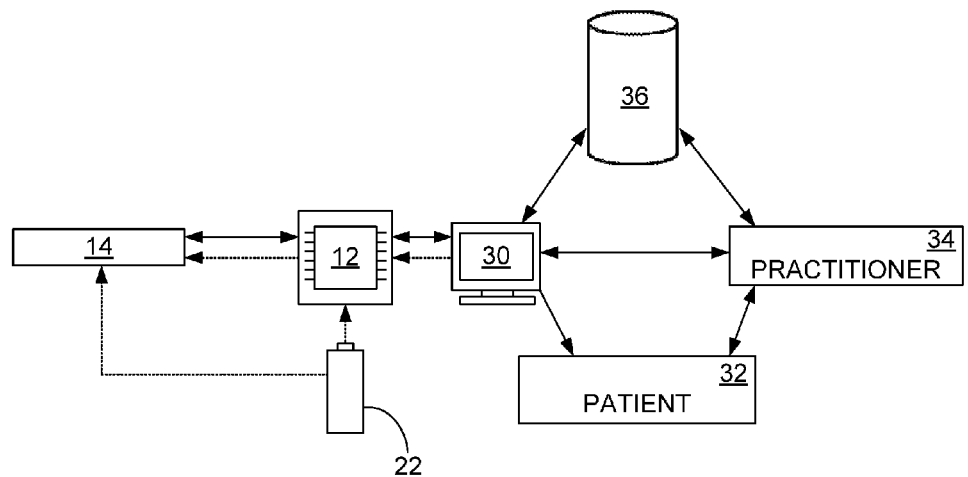
FIG. 8 is a schematic layout indicating various ways of collecting data related to a patient's response to the apparatus.

The configuration shown by the diagram in FIG. 8 makes it possible for a practitioner (34) to receive real-time feedback and information regarding the stimuli (forces and moments) applied to a patient's teeth as well as the effect that these stimuli have on the affected tissues. In addition, such data can be gathered over a long period of time, which would enable the practitioner (34) to analyse the biomechanical response that takes place for a particular patient (32) between visits, as well as compare the responses to those of other patients stored on the database (36). The bi-directional information exchange between the practitioner (34) and the apparatus can be direct, over a physical connection when the patient is in the presence of the practitioner, but can also take place by other, remote means, such as over the Internet or other suitable telecommunications network. This will enable the practitioner (34) to monitor patient (32) data as well as to make treatment decisions and upload new force profiles or make adjustments to existing force profiles without the need for the patient to be in the presence of the practitioner. In addition, it would be possible to allow the patient (32) to access information regarding his or her progress and, where necessary, create programs to improve patient compliance.

By making use of a sensor system and feedback to a central processing unit, the present invention is capable of generating valuable data regarding the application of various stimuli to the teeth or other parts of the dento-oral complex and how these affect the underlying biomechanical processes. The availability of such information may be valuable to researchers and may be shared between practitioners on a global level by means of systems such as those described with reference to FIG. 8. Global databases such as those described could be used to collect patient, age and/or case-specific data generated by the feedback of the system and apparatus of the invention, which in turn could be used to develop more advanced biomechanical models; something that a number of research programs have, according to the applicant's knowledge, failed to succeed in.

Figure 9:
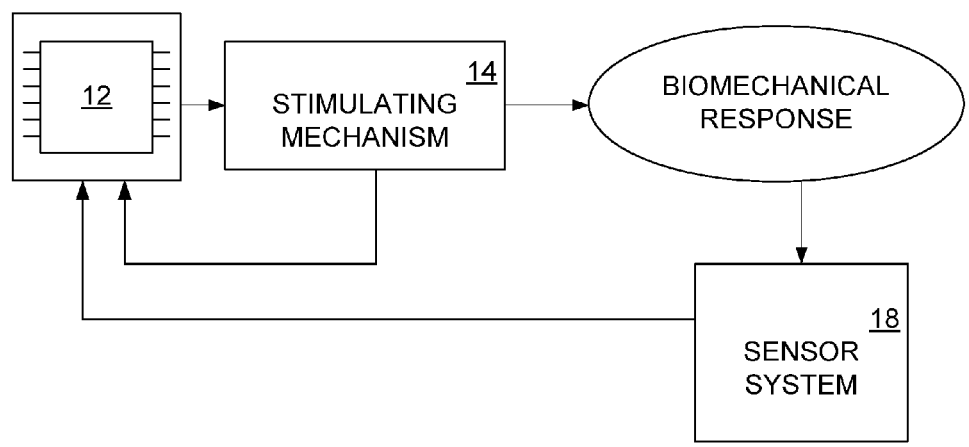
FIG. 9 is a schematic layout of a direct feedback system in accordance with the invention.

The apparatus and system of the invention may be used to determine the optimal forces and moments that should be applied to specific teeth, or other parts of the dento-oral complex, of a patient so as to allow a practitioner to manually adjust the apparatus, or even a more commonly available apparatus, to apply these optimal forces and moments. The apparatus of the invention may, however, also be used to automatically adjust the forces and moments applied so as to be increasingly representative of an optimal force profile. Such an automatically adjusting apparatus is shown in more detail in FIG. 9. The figure shows a direct feedback system incorporated into the apparatus. As before, the processor (12) submits control signals to the stimulator (14). The stimulator (14) in turn responds to the control signals, by causing the actuators to exert a force or moment onto a tooth or a part of the dento-oral complex. This in turn triggers a biomechanical response of which the parameters are measured by a sensor (18). The sensor (18) then sends these parameters back to the processor (12), which in turn determines whether the required biomechanical response is taking place. Based on prior recorded parameters and or algorithms programmed on it the processor may then alter the control signals to alter the forces applied by the actuators in order to be increasingly representative of the optimal orthodontic force. Such a direct feedback system may be necessary to ensure the correct biomechanical response, as the response to a specific force may vary between different patients.

Figure 10:
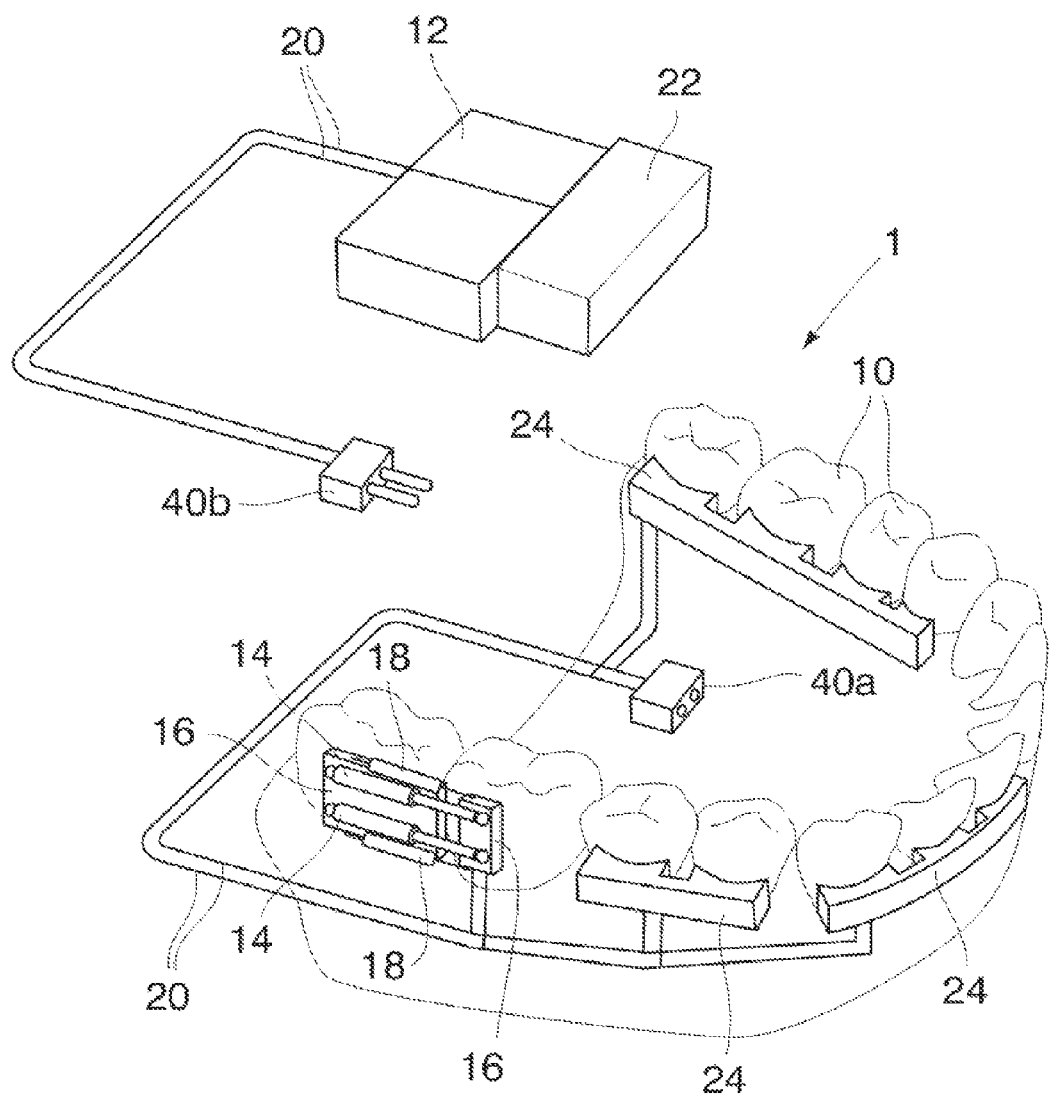
FIG. 10 is a perspective view of a yet further embodiment of the invention.

FIG. 10 shows a further embodiment of an apparatus (1) in accordance with the invention. As before, like features described above with reference to FIGS. 1 and 7 are indicated with like reference numerals. In this embodiment, the processing unit (12), power source (22) or both are able to be removed from the device in its operative position, and are connectable to the apparatus by means of a connection point or plug (40). This may reduce the space needed by the apparatus inside the mouth of a patient. If only the processor (12) can be removed from the apparatus, it may be possible for the actuators (14) to apply a stable, unchanging force as was previously instructed by the processor until the processor is again connected to it at a later stage at which stage a different control signal may be applied. It may therefore be possible for the processor to be inserted periodically, whether at fixed or irregular intervals, to enable possible corrections to the applied forces to be made. If the power source (22) is removable, it may be possible for the stimulators (14) to lock in a fixed position when the power is disconnected, thus ensuring a relative constant force to be applied by the stimulators (14) for as long as the power source remains disconnected. Alternatively, the power source (22), processor (12) or both may be positioned extra-orally instead of intra-orally.

One of the limitations of conventional orthodontics is the unavailability of biomechanical feedback and thus a disregard of the underlying biological processes which facilitate bone remodelling and tooth movement such as the localised pressure in the PDL. Typically, braces are placed and left until a follow up visit to the practitioner, when changes to the dental structures are examined visually and adjustments to the braces made if deemed necessary. During the times between patient visits there is a complete lack of information regarding the relationship between the stimulus applied and the biomechanical tissue response resulting from such a stimulus, both long and short term. Even though the practitioner is able to observe tooth movement, it may be possible that the biomechanical process by which this movement occurred was less than optimal. For example, if an excessive pressure was applied to the PDL, bone remodelling may have occurred by means of undermining resorption, instead of the preferred frontal resorption.

As briefly mentioned above, the apparatus or system of the invention may also be used only for initial evaluation of, for example, a person's specific biological response to the application of various forces. This may provide an expected profile of teeth movement based on gathered data or other calculations. This would allow a different system or method to be used to correct a patient's dento-oral complex.

It should be appreciated that the above description is by way of example only and that numerous modifications may be made to the embodiments of the invention described without departing from the scope of the invention. In particular, it is foreseen that the invention may also be used, possibly in a slightly altered or specialised way, in orthopaedic processes for the remodelling or reconstruction of bone and tissue other than that relating to the dento-oral complex.

The invention claimed is:

1. A medical apparatus for use in the corrective treatment of malocclusion or other dento-facial defects comprising:
   at least one stimulator configured to apply a stimulus to a part of the dento-oral complex utilising at least one actuator the actuator being controllable by means of electronic control signals;
   attachment formations configured to secure the at least one stimulator to the part of the dento-oral complex;
   a closed loop feedback system including at least one sensor configured to measure parameters relating to biomechanical tissue response resulting from the stimulus applied by the stimulator;
   a power source configured to provide power to the apparatus; and
   a processor in data communication with the stimulator and closed loop feedback system, wherein the processor is configured to receive the parameters from the closed loop feedback system, process the received parameters with reference to a desired biomechanical tissue response and adjust the control signals based at least to some extent on the processed parameters, and to transmit the adjusted control signals to the stimulator so that the stimulus applied by the stimulator as a result of the adjusted control signals are increasingly representative of an optimal orthodontic force.

2. A medical apparatus as claimed in claim 1 wherein the control signals cause the stimulator to apply stimuli varying in one or more of magnitude, frequency, direction, duration and point of application.

3. A medical apparatus as claimed in claim 1 wherein the at least one sensor is configured to sense a change in pressure, force or position of a tooth or other part of the dento-oral complex.

4. A medical apparatus as claimed in claim 3 wherein the at least one sensor is configured to sense a change in tooth movement occurring over a period of time.

5. A medical apparatus as claimed in claim 1 wherein the processor includes a memory module in data communication with it and on which is stored software configured to cause the processor to receive parameters from the sensors, to store and process the parameters, to adjust the control signals and to transmit the control signals to the stimulator.

6. A medical apparatus as claimed in claim 5 which includes a communication module enabling it to communicate with an external processor.

7. A medical apparatus as claimed in claim 6 wherein the communication module is configured to communicate over a local area or wide area network or the Internet and is connectable to a communications network by means of one or more of a Universal Serial Bus port, an infra-red module, a Bluetooth module and a near-field communication module.

8. A medical apparatus as claimed in claim 6 wherein the software is uploaded to the memory module by means of the communication module.

9. A medical apparatus as claimed in claim 6 wherein parameters received by the processor and stored on the memory module are uploaded to a computer via the communication module.

10. A medical apparatus as claimed in claim 9 wherein the parameters are uploaded to a remote database associated with the computer for archiving and/or further processing.

11. A medical apparatus as claimed in claim 1 wherein the apparatus is provided with waterproof, protective housings configured to enable the apparatus to operate intra-orally.

12. A medical apparatus as claimed in claim 1 wherein the power source and processor are detachable.

13. A medical apparatus as claimed in claim 12 wherein the at least one actuator is configured to exert a stable force when the power source or the processor has been detached.

14. A medical apparatus as claimed in claim 1 in which the processor is further configured to monitor and record the parameters over a period of time and for a number of different forces and moments, and to determine an optimal orthodontic force based at least partially on the recorded parameters and their corresponding applied forces and moments.

15. A system for use in the corrective treatment of malocclusion or other dento-facial defects comprising a plurality of medical apparatuses as claimed in claim 1, wherein the plurality of medical apparatuses are controlled by at least one central processor.

16. A system as claimed in claim 15 which includes a central communications module operable to communicate recorded data to and from a remotely accessible system database.

17. A method of determining an optimal force for application to a part of the dento-oral complex of a patient for the corrective treatment of malocclusion and other dento-facial defects, the method including the steps of:

applying a stimulus to the part of the dento-oral complex of the patient;

collecting with at least one sensor, parameters relating to the movement of the part of the dento-oral complex resulting from the application of the stimulus;

transmitting the parameters to a processor in data communication with the at least one sensor;

analysing the parameters with reference to a desired biomechanical tissue response stored in a memory associated with the processor;

repeatedly adjusting the applied stimulus based on the analyses and collecting further parameters relating to the movement of the part of the dento-oral complex resulting from the application of the adjusted stimulus; and identifying the stimulus being applied as the optimal force if optimal movement of the part of the dento-oral complex is achieved by application of the stimulus.

18. A method of treating malocclusion and other dento-facial defects in patients in need of treatment, the method including the steps of:

applying a predetermined stimulus to a part of the dento-oral complex of the patient;

collecting by way of at least one sensor, parameters relating to the movement of the part of the dento-oral complex resulting from the application of the stimulus;

transmitting the parameters to a processor in data communication with the at least one sensor;

analysing the parameters with reference to a desired biomechanical tissue response stored in a memory associated with the processor; and repeatedly adjusting the applied stimulus based on the analyses and collecting further parameters relating to the movement of the part of the dento-oral complex resulting from the application of the adjusted stimulus until optimal movement of the part of the dento-oral complex to which the stimulus is applied is achieved.

* * * * *